United States Patent [19]

Pernicka

[11] Patent Number: 5,131,737
[45] Date of Patent: Jul. 21, 1992

[54] PROTECTIVE ACCESSORY FOR SPORT SPECTACLES

[75] Inventor: Martin Pernicka, Montréal, Canada

[73] Assignee: Leader Sport Products Canada, Inc., Quebec, Canada

[21] Appl. No.: 566,176

[22] Filed: Aug. 10, 1990

[51] Int. Cl.$^5$ .......................... G02C 1/00; G02C 5/12
[52] U.S. Cl. ...................... 351/88; 351/138; 351/139
[58] Field of Search ............ 351/41, 80, 88, 132, 351/138, 139

[56] References Cited

U.S. PATENT DOCUMENTS 3,584,939  6/1971  Olson .................................. 351/132

Primary Examiner—Rodney B. Bovernick
Attorney, Agent, or Firm—Quarles & Brady

[57] ABSTRACT

The disclosure herein describes a protective accessory for mounting to the frame of sport spectacles, which is formed of a body made of resilient material and includes a bow-covering central portion and frame engaging extensions integral with the central portion on opposite sides thereof. The central portion has an opening extending transversally therethrough. The material is stretchable to allow endwise insertion of an eyeglass section through the opening until the bow of the frame is received within the central portion of the body with the extensions engaging corresponding frame portions of the eyeglass sections.

11 Claims, 1 Drawing Sheet

U.S. Patent   July 21, 1992   5,131,737
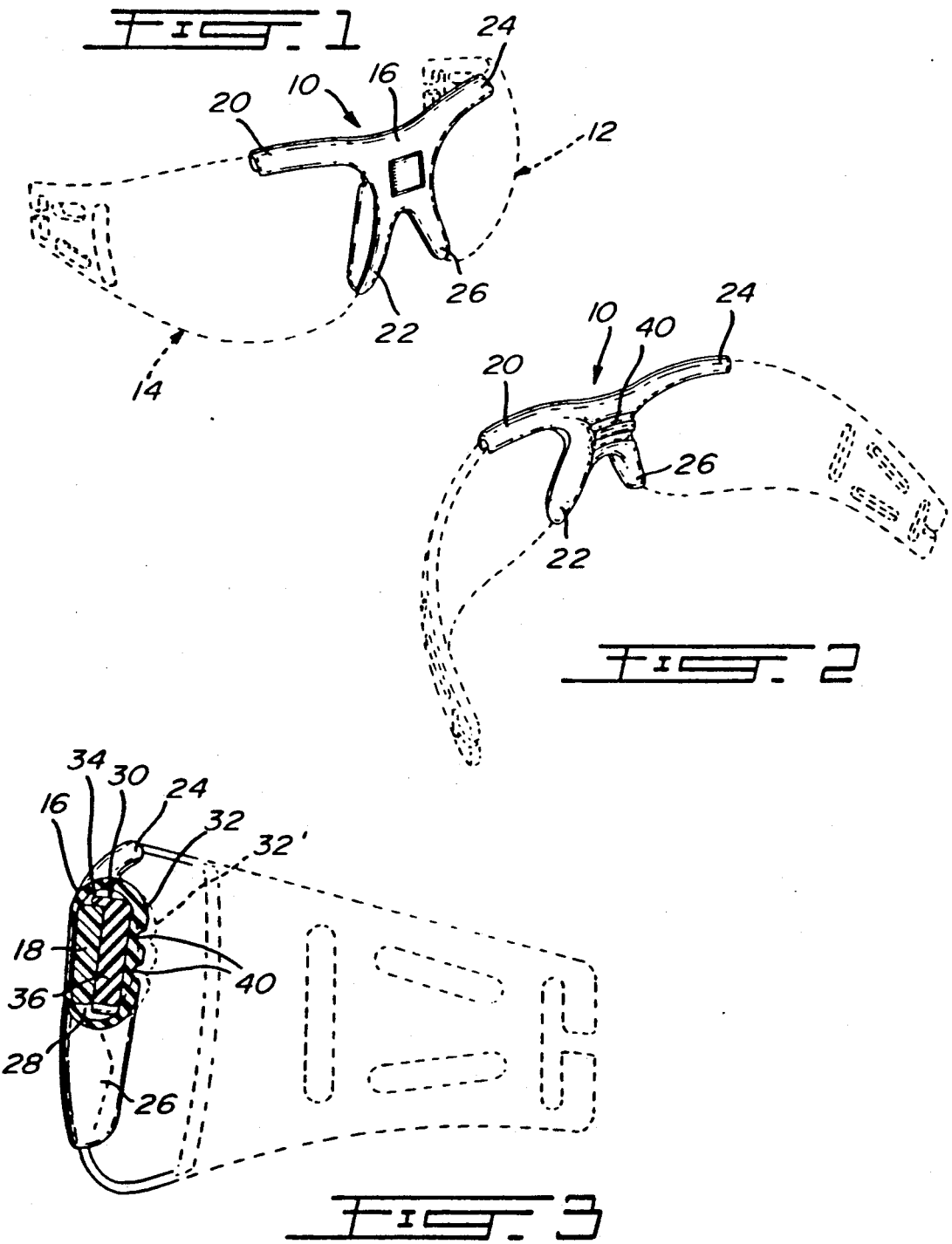

1

PROTECTIVE ACCESSORY FOR SPORT SPECTACLES

FIELD OF THE INVENTION

The present invention relates to a protective accessory for mounting to the frame of sport spectacles.

BACKGROUND OF THE INVENTION

In Various sports where spectacles or goggles are used, serious damages can be done to a user's eyes, nose or eyebone structure whenever the spectacles or goggles are accidently contacted or subjected to hard impact. At present, some protective devices are used on spectacles. They are permanently fixed to the spectacles, either moulded therewith, or consisting of two parts glued to one another and/or to the frame structure.

OBJECTS AND STATEMENT OF THE INVENTION

It is an object of the present invention to provide a protective accessory adapted to be separately mounted to the frame of sports spectacles or the like.

It is a further object of the present invention to provide such protective accessory which, during assembly, can be easily and quickly installed to the central nose-covering bow of spectacles.

It is a further object of the present invention to provide such a protective accessory for sport spectacles which may be adapted to various configurations of noses.

Still, it is an object of the present invention to provide a protective accessory which is confortable, allowing air circulation between the accessory and the user's skin.

This is achieved by providing a protective accessory for mounting to the frame of sport spectacles which comprises: a body made of resilient material which includes a bow-covering central portion and frame engaging extensions integral with the central portion on opposite sides thereof, the central portion having an opening extending transversally therethrough. The material is stretchable to allow endwise insertion of an eyeglass section of the spectacles through the opening until the bow of the frame is received within the central portion of the body with the side extensions engaging corresponding frame portions of the eyeglass sections.

In one preferred form of the invention, pads may also be inserted in the central opening, the pads having configurations to conform with the varying configurations of the bridge of a user's nose. These pads assist in distancing the spectacles from the user's eyes to reduce condensation on the eyeglasses.

In a further preferred form of the invention, the rear portion of the body which contacts the user's skin is provided with air circulation channels.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

FIG. 1 is a front perspective view of the protective accessory made in accordance with the present invention being mounted on spectacles (shown in dotted lines);

FIG. 2 is a rear perspective view thereof; and

FIG. 3 is a cross-sectional view through the central bow-covering portion.

DESCRIPTION OF PREFERRED EMBODIMENTS

Referring to the figures, there is shown a protective accessory, generally denoted 10, for mounting to the frame of sport spectacles displaying a pair of eyeglass sections 12 and 14. Each of these eyeglass sections may include a frame in which is received a fixed or removable eyeglass or, especially in cases of plastic eyeglasses, the frame forms an integral part with the transparent viewing areas of the spectacles. One suitable plastic for spectacles is polycarbonate. Therefore, the present invention is not limited to a particular construction of spectacles.

The accessory 1 comprises a central portion 16 10 which covers the bow 18 (see FIG. 3) interconnecting the eyeglass sections of the spectacles. The body of the accessory is X-shaped defining pairs of opposite side extensions 20, 22 and 24, 26. All extensions are grooved to snuggly fit over and engage portions of the frames of the eyeglass sections.

Referring more particularly to FIG. 3, section 16 of the accessory has a central opening 28 through which extends the bow 18 of the frame of the spectacles. The material of body 10 is manually stretchable so that opening 28 may be enlarged to allow endwise insertion of the accessory to an opposite side of the eyeglass sections 12 and 14. A suitable material is one made of a silicone, preferrably transparent, to allow viewing of the frame engagement with the accessory.

In a further form of the invention, a pad 30 is inserted in the opening 28 between the bow 18 and the rear portion 32 of the bow covering central portion 16. This pad 30 is made of resilient material (i.e. silicone) and includes an upper horizontal portion 34 adapted to rest on the top wall of the bow 18 and of a vertical portion 36 having a front face contacting the bow 18 and an opposite rear face contacting the rear portion of the bow-covering portion 16.

Dotted lines 32' serve to illustrate that the said rear face of the pad may have a different thickness to give a varying shape to that portion of the accessory which contacts the wearer's nose. Hence, the resiliency of the body allows the user to stretch the bow covering portion to remove one insert and replace it with another of varying size to fit a particular nose configuration.

As an additional feature of the present invention, the rear portion 32 of the body is provided with one or more horizontal channels 40 to reduce the contact surface with the wearer's skin to facilitate air circulation therebetween.

Although the invention has been described above with respect to various forms, it will be evident to a person skilled in the art that it may be modified and refined in various ways. It is therefore wished to have it understood that the present invention should not be limited in scope, except by the terms of the following claims.

The embodiments of the invention in which an exclusive property or privilege is claimed are defined as follows:

1. A protective accessory for mounting to the frame of sport spectacles, the frame including a nose-covering central bow interconnecting a pair of eyeglass sections, comprising:

a body made of resilient material including a bow-covering central portion and frame-engaging extensions integral with said central portion on opposite sides thereof;

said central portion having an opening extending transversely therethrough; said frame-engaging extension including a first set of top extensions extending from said central portion above said opening and a second set of bottom extension extending from said central portion below said opening; said material being stretchable so as to allow endwise insertion of an eyeglass section through said opening until the bow of the frame is received within said central portion of said body with said first and second set of extensions engaging corresponding frame portions of said eyeglass sections.

2. A protective accessory as defined in claim 1, wherein said second set of bottom extension extend substantially downwardly to engage facing surfaces of said eyeglass sections.

3. A protective accessory for mounting to the frame of sport spectacles, the frame including a nose-covering central bow interconnecting a pair of eyeglass sections, comprising:

a body made of resilient material including a bow-covering central portion and frame-engaging extensions integral with said central portion on opposite sides thereof;

said central portion having an opening extending transversely therethrough; said frame-engaging extensions including a first set of top extensions extending from said central portion above said opening and a second set of bottom extensions extending from said central portion below said opening; said material being stretchable so as to allow endwise insertion of an eyeglass section through said opening until the bow of the frame is received within said central portion of said body with said first and second set of extensions engaging corresponding frame portions of said eyeglass sections, and further comprising pad means disposed in said bow-covering central portion between said central bow and that portion of said body adapted to contact users knows.

4. A protective accessory as defined in claim 3, wherein said pad means are removably mounted in said opening.

5. A protective accessory as defined in claim 3 or claim 4, wherein an outer face of that portion of the body contacting a user's nose displays air circulation channel means thereon.

6. A protective accessory as defined in one of claims 1, 3 or 4, wherein said body is X-shaped with four side extensions engaging corresponding frame portions of said eyeglass sections.

7. A protective accessory as defined in claim 6, wherein said extensions are grooved to tightly engage said corresponding frame portions of said eyeglass sections.

8. A protective accessory as defined in claim 1, 3 or 4 wherein said material is a silicone.

9. A protective accessory as defined in claim 8, wherein said silicone is transparent.

10. A protective accessory as defined in claim 3, wherein said pad means includes an upper horizontal portion resting on said bow and a vertical portion extending between said bow and a rear portion of said central portion adapted to contact a user's nose.

11. In combination, a protective accessory for mounting to the frame of sport spectacles and said frame including a nose-covering central bow interconnecting a pair of eyeglass sections, said protective accessory comprising:

a body made of resilient material including a bow-covering central portion and frame-engaging extension integral with said central portion on opposite sides thereof;

said central portion having an opening extending transversely therethrough;

said material being stretchable so as to allow endwise insertion of an eyeglass section through said opening until the bow of the frame is received within said central portion of said body width, said extensions engaging corresponding frame portions of eyeglass sections.

* * * * *